United States Patent [19]

Iwasaki et al.

[11] Patent Number: 5,342,941
[45] Date of Patent: Aug. 30, 1994

[54] NAPHTHALENE DERIVATIVES, PROCESSES FOR PREPARING THE SAME, AND SYNTHETIC INTERMEDIATES THEREFOR

[75] Inventors: Tameo Iwasaki, Nishinomiya; Kazuhiko Kondo, Osaka; Katsuo Ikezawa, Urawa; Hideo Kikkawa, Okegawa; Shinsuke Yamagata, Osaka, all of Japan

[73] Assignee: Tanabe Seiyaku Co., Ltd., Osaka, Japan

[21] Appl. No.: 19,885

[22] Filed: Feb. 19, 1993

[30] Foreign Application Priority Data

Feb. 20, 1992 [JP] Japan .................. 4-085118

[51] Int. Cl.$^5$ ............................................. A61K 31/44
[52] U.S. Cl. ...................... 514/337; 514/247; 514/327; 514/340; 514/345; 544/239; 546/205; 546/275; 546/269; 546/301; 546/302; 546/341; 546/344; 546/342; 540/302; 540/341; 540/344; 540/342; 568/592; 546/290; 562/512
[58] Field of Search ............... 546/301, 344, 341, 302; 514/345, 327

[56] References Cited

U.S. PATENT DOCUMENTS

| | | | |
|---|---|---|---|
| 4,503,061 | 3/1985 | Bristol | 546/301 |
| 4,590,200 | 5/1986 | Cross | 546/302 |
| 4,661,596 | 4/1987 | Kreft, III et al. | 546/152 |
| 4,792,556 | 12/1988 | Murthy | 546/301 |
| 5,068,394 | 11/1991 | Andree et al. | 546/302 |
| 5,182,296 | 1/1993 | Nakai et al. | 548/231 |
| 5,189,047 | 2/1993 | Hadley et al. | 546/301 |
| 5,208,246 | 5/1993 | Almansa et al. | 546/302 |
| 5,272,170 | 12/1993 | Almansa et al. | 548/482 |

FOREIGN PATENT DOCUMENTS 0313296 4/1989 European Pat. Off. .
0347027 12/1989 European Pat. Off. .

OTHER PUBLICATIONS

D. N. Reinhoudt et al., "A Novel Route for the Synthesis of Benzo[b]thiepins,"*Tetrahedron*, 30, 2431–2436 (1974).
A. Sakurai et al., "The Cyclization of Ethyl Acetoacetate and Ketones by Ammonium Acetate," *Bull. Chem. Soc. Japan 41*, 165–167 (1968).

*Primary Examiner*—Donald G. Daus
*Attorney, Agent, or Firm*—Finnegan, Henderson, Farabow, Garrett & Dunner

[57] ABSTRACT

Naphthalene derivative of the formula [I]:

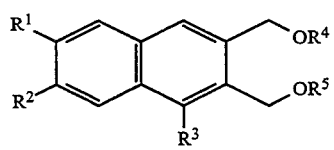

wherein $R^1$ and $R^2$ are the same or different and are hydrogen atom, hydroxy group, cyclo-lower alkyloxy group, substituted or unsubstituted lower alkoxy group, or both combine each other to form lower alkylenedioxy group, $R^3$ is substituted or unsubstituted nitrogen-containing 6-membered heterocyclic group, and groups of the formulae: —$OR^4$ and —$OR^5$ are the same or different and are protected or unprotected hydroxy group, processes for preparing thereof, and synthetic intermediates therefor, these compounds have excellent bronchodilating activity, and are useful in the prophylaxis and treatment of asthma.

9 Claims, No Drawings

NAPHTHALENE DERIVATIVES, PROCESSES FOR PREPARING THE SAME, AND SYNTHETIC INTERMEDIATES THEREFOR

The present invention relates to a novel naphthalene derivative having an antiasthmatic activity, processes for preparing the same, and synthetic intermediates therefor.

PRIOR ART

Although there has been known as a naphthalene derivative having a nitrogen-containing 6-membered heterocyclic group at the 1-position, 1-(5-methyl-2(1H)-pyridon-3-yl)naphthalene [cf. Bulletin of The Chemical Society of Japan, Vol. 41, 165-167 (1968)], the pharmaceutical use and activities thereof have never been known yet. On the other hand, many antiasthmatics have been known, but conventional antiasthmatics have various deficits, for example, they do not show sufficient inhibitory action on bronchoconstriction, or they cannot overcome serious side effects on heart, and the like.

Under such circumstances, the present inventors intensively have studied, and have found novel naphthalene compounds having antiasthmatic activity, of which structures are different from those of the conventional compounds having antiasthmatic activity, and have accomplished the present invention.

SUMMARY DESCRIPTION OF THE INVENTION

An object of the present invention is to provide novel naphthalene derivatives of the formula [I]:

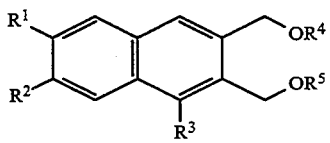

wherein $R^1$ and $R2$ are the same or different and are hydrogen atom, hydroxy group, a cyclo-lower alkyloxy group, a substituted or unsubstituted lower alkoxy group, or both combine each other to form a lower alkylenedioxy group, $R^3$ is a substituted or unsubstituted nitrogen-containing 6-membered heterocyclic group, and groups of the formulae: $—OR^4$ and $—OR^5$ are the same or different and are a protected or unprotected hydroxy group, or a pharmaceutically acceptable salt thereof.

Another object of the invention is to provide processes for preparing the compounds [I] or a pharmaceutically acceptable salt thereof.

The other object of the invention is to provide synthetic intermediates therefor.

DETAILED DESCRIPTION OF THE INVENTION

The desired compounds [I] of the present invention and pharmaceutically acceptable salts thereof have potent bronchodilating activity, and are useful as medicines in the prophylaxis and treatment of asthma. For instance, the desired compounds [I] show potent inhibitory activity on bronchoconstriction, e.g. 3 to 100 times stronger than that of theophylline, without showing any side effects on heart.

Suitable examples of the desired compounds [I] of the present invention are the compounds of the formula [I], wherein $R^3$ is pyridyl group, N-oxypyridyl group, 2(1H)-pyridonyl group, 4,5-dihydro-3(2H)-pyridazinonyl group or 3(2H)-pyridazinonyl group, which may be substituted by a halogen atom (e.g. fluorine, etc.), or 2-alkoxypyridyl group or N-alkyl-2(1H)-pyridonyl group, in which said alkoxy group and alkyl group may optionally be substituted by a group selected from hydroxy group, a lower alkoxy group, a lower alkoxy-lower alkoxy group, a lower alkylthio group, a lower alkenyl group, cyano group, carboxyl group, a lower alkoxycarbonyl group, carbamoyl group, a di-lower alkylamino group, a lower alkanoyl group, phenyl group, furyl group, tetrahydrofuryl group and oxazolyl group.

Other examples of the desired compounds [I] of the present invention are the compounds of the formula [I], wherein $R^1$ and $R^2$ are (1) hydrogen atom, (2) hydroxy group, (3) a cyclo-lower alkyloxy group, or (4) a lower alkoxy group which may optionally be substituted by a group selected from hydroxy group, a lower alkoxy group, a lower alkoxy-lower alkoxy group, a lower alkoxycarbonyl group and phenyl group, or (5) both combine each other to form a lower alkylenedioxy group.

The pharmaceutically preferable compounds [I] are the compounds of the formula [I], wherein $R^1$ and $R^2$ are the same or different and are a lower alkoxy group, and $R^3$ is pyridyl group, N-alkyl-2(1H)-pyridonyl group or N-(lower alkoxy-lower alkyl)-2(1 H)-pyridonyl group.

Among the desired compounds [I] of the present invention, groups of the formulae: $—OR^4$ and/or $—OR^5$ are either hydroxy group or a hydroxy group protected by any pharmaceutically acceptable groups. The hydroxy-protecting group may be any ones which are removed by hydrolysis, etc. in living body, and do not produce any harmful side products. Suitable examples of the protected hydroxy group are hydroxy groups protected by a lower alkanoyl group or a lower alkyl group.

The desired compounds [I] of the present invention can be used as a medicine either in the free form or in the form of pharmaceutically acceptable salt thereof. For example, since the desired compounds [I] have a nitrogen-containing 6-membered heterocyclic group at the 1-position of the naphthalene nucleus, they can be used in the form of an organic or inorganic acid addition salt thereof. Further, when the desired compounds [I] have a substituent such as carboxyl group on the nitrogen-containing 6-membered heterocyclic group, they can be used in the form of a basic salt thereof.

The pharmaceutically acceptable salts are, for example, salts with inorganic acids (e.g. hydrochloride, sulfate, hydrobromide, etc.), salts with organic acids (e.g. acetate, fumarate, oxalate, etc.), alkali metal salts (e.g. sodium salt, potassium salt, etc.) or alkaline earth metal salts (e.g. calcium salt, etc.).

The desired compounds [I] of the present invention and pharmaceutically acceptable salts thereof can be administered either orally or parenterally, and administered in the form of conventional pharmaceutical preparations such as tablets, granules, capsules, powder, injection forms and inhalants.

The dosage of the desired compounds [I] of the present invention and pharmaceutically acceptable salts thereof varies depending on administration route, age, weight and conditions of the patients, but it is usually in the range of about 0.01 to 30 mg/kg/day, preferably about 0.1 to 10 mg/kg/day.

According to the present invention, the desired compounds [I] of the present invention can be prepared by any one of the following Process A to Process D.

PROCESS A

The desired compounds [I] of the present invention can be prepared by subjecting a compound of the formula [II]:

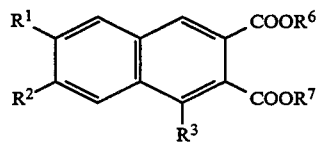

wherein $R^1$ and $R^2$ are the same or different and are hydrogen atom, hydroxy group, a cyclo-lower alkyloxy group, a substituted or unsubstituted lower alkoxy group, or both combine each other to form a lower alkylenedioxy group, $R^3$ is a substituted or unsubstituted nitrogen-containing 6-membered heterocyclic group, and groups of the formulae: —COOR$^6$ and —COOR$^7$ are a free carboxyl group or esterified carboxyl group, or an internal anhydride thereof, to reduction to give a compound of the formula [I-a]:

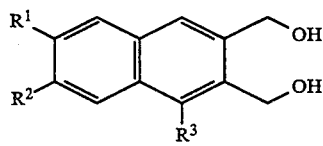

wherein the symbols are the same as defined above, if necessary, followed by protecting the 2- and/or the 3-hydroxymethyl moieties.

PROCESS B

Among the desired compounds [I] of the present invention, the compounds of the formulae [I-c] and [I-d]:

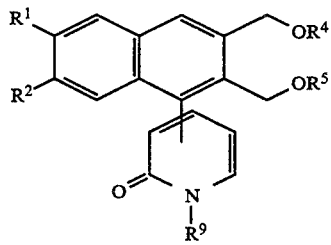

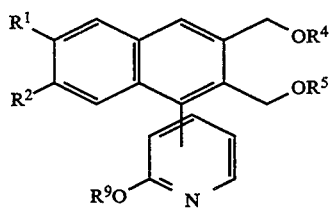

wherein $R^9$ is a substituted or unsubstituted lower alkyl group, and the other symbols are the same as defined above, can be prepared by reacting a compound of the formula [I-b$_1$]:

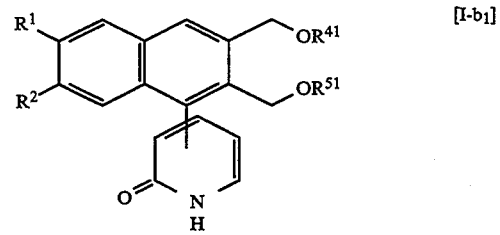

wherein groups of the formulae: —OR$^{41}$ and —OR$^{51}$ are protected or unprotected hydroxy-group, and the other symbols are the same as defined above, with a compound of the formula [III]:

$$X—R^9 \quad [III]:$$

wherein X is a halogen atom and $R^9$ is the same as defined above, to give compounds of the formulae [I-c$_1$] and [I-d$_1$]:

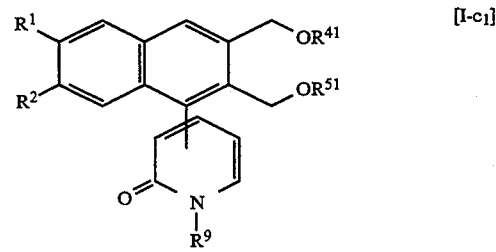

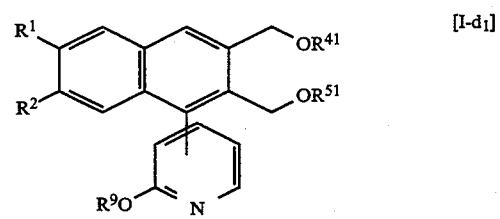

wherein the symbols are the same as defined above, and when the groups of the formulae: —OR$^{41}$ and/or —OR$^{51}$ are a protected hydroxy group, if necessary, followed by removing the protecting group for said hydroxy groups, and further if necessary, by protecting again the 2- and/or 3-hydroxymethyl moieties.

PROCESS C

Among the desired compounds [I], the compound of the formula [I-c]:

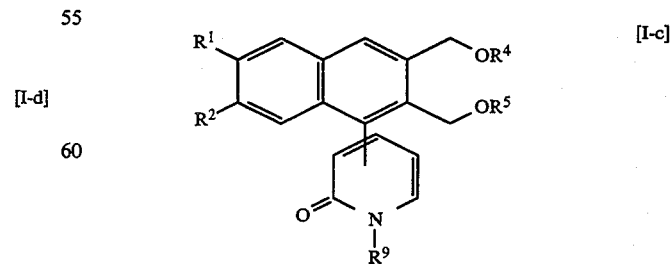

wherein the symbols are the same as defined above, can also be prepared by subjecting a compound of the formula [I-e$_1$]:

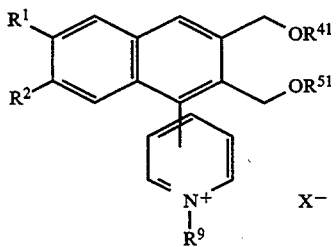

wherein the symbols are the same as defined above, to oxidation to give a compound of the formula [I-c₁]:

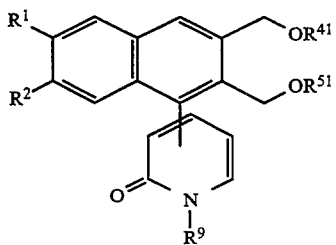

wherein the symbols are the same as defined above, when the groups of the formulae: —OR⁴¹ and —OR⁵¹ are a protected hydroxy group, if necessary, followed by removing the protecting group for said hydroxy groups, and further if necessary, by protecting again the 2- and/or 3-hydroxymethyl moieties.

PROCESS D

Among the desired compounds [I], the compound of the formula [I-h]:

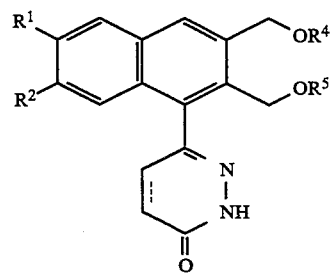

wherein the dotted line means single bond or double bond, and the other symbols are the same as defined above, can be prepared by reacting a compound of the formula [IV]:

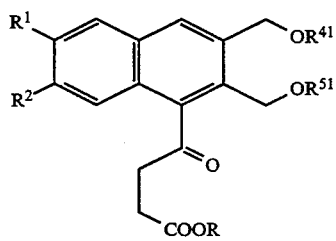

wherein the group of the formula: —COOR is a free carboxyl group or an esterified carboxyl group, and the other symbols are the same as defined above, with hydrazine to give a compound of the formula [I-f]:

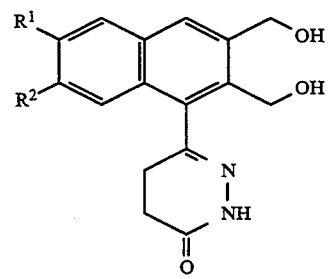

wherein the symbols are the same as defined above, if necessary, followed by subjecting the compound [I-f] to oxidation to give a compound of the formula [I-g]:

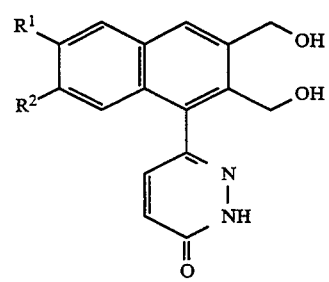

wherein the symbols are the same as defined above, and if necessary, further by protecting the 2- and/or 3-hydroxymethyl moieties of the compound [I-f] or [I-g].

These processes A to D can be carried out as follows.

Process A

The reduction reaction of the starting compound [II] or an internal anhydride thereof can be carried out using a suitable reducing agent in a suitable solvent. The esterified carboxyl group of the starting compound [II] may be any one which can be converted into hydroxymethyl group by the reduction reaction, and includes, for example, a lower alkoxycarbonyl group. The reducing agent may be selected according to the types of $R^6$ and $R^7$. For instance, when $R^6$ and/or $R^7$ are an ester residue, the reducing agent is, for example, lithium aluminum hydride, sodium bis(methoxyethoxy)aluminum hydride, sodium borohydride, and among which sodium bis(methoxyethoxy)aluminum hydride is preferable. On the other hand, when $R^6$ and/or $R^7$ are hydrogen atom, lithium aluminum hydride is preferably used as a reducing agent. Further, the internal anhydride of the compound [I] can be prepared by subjecting the compound [I] wherein $R^6$ and $R^7$ are hydrogen atom, to internal dehydration reaction. The reduction of said internal anhydride compound is carried out under the same conditions as the reduction reaction of the compound [II] wherein $R^6$ and/or $R^7$ are hydrogen atom. These reduction reactions can be carried out in a suitable solvent such as ethers (e.g. tetrahydrofuran, diethyl ether, dioxane, etc.) under cooling or heating.

Process B

The condensation reaction between the compounds I-b₁] and [III] can be carried out in the presence of a base in a suitable solvent. The base includes, for example, sodium hydride, lithium hydride, lithium diisopropylamide, potassium bis(trimethyl)amide, and the like, and the solvent includes, for example, dimethylformamide, and the like.

The desired compounds [I-c] and [I-d] obtained in Process B can be separated by a conventional method such as chromatography (e.g. silica gel chromatography, etc.).

Process C

The oxidation reaction of the compound [I-e₁] can be carried out in a suitable solvent by a conventional method. The oxidizing agent includes, for example, dicyanodichloroquinone, potassium ferricyanide, and the like, among which potassium ferricyanide is preferable. The solvent may be any one which does not affect the reaction, and includes, for example, dioxane, water, methanol, ethanol, and the like. The reaction is preferably carried out under cooling or at room temperature.

Process D

The reaction between the compound [IV] and hydrazine can be carried out in a suitable solvent. Hydrazine is preferably hydrazine hydrate. The solvent may be any one which does not affect the reaction, and includes, for example, methanol, ethanol, tetrahydrofuran, dimethylformamide, and the like. The reaction is preferably carried out with warming or heating. When the compound [IV], wherein the 2- and/or 3-positions are a protected hydroxy group, is used in this reaction, the said protecting groups for hydroxy group are removed simultaneously.

The oxidation of the compound [I-f] can be carried out using an oxidizing agent in a suitable solvent. The oxidizing agent is preferably dicyanodichloroquinone, and the like. The solvent may be any one which does not affect the reaction, for example, dioxane, methanol, ethanol, water, and the like. The reaction is preferably carried out under cooling or at room temperature.

In the above Processes B and C, when the groups of the formulae: —OR⁴¹ and/or —OR⁵¹ are a protected hydroxy group, the removal of the said protecting group from the products can be carried out by a conventional method, which is selected according to the types of the protecting groups to be removed, for example, hydrolysis, acid treatment, reduction, and the like. Moreover, in the above Processes A to D, the protection of the 2- and/or 3-hydroxymethyl moieties can be carried out by a conventional method, for example, by subjecting the OH-unprotected product to condensation reaction with a reactive derivative of the protecting group corresponding to R⁴ and R⁵, e.g. acid anhydride of a lower alkanoic acid, acid halide, a lower alkyl halide, etc. The reaction is preferably carried out in the presence or absence of a basic compound (e.g. triethylamine, pyridine, dimethylaminopyridine, sodium hydride, etc.) in a suitable solvent (e.g. methylene chloride, etc.) or without a solvent. Since the 3-hydroxymethyl moiety is more reactive than the 2-hydroxymethyl moiety, when a reactive derivative of the protecting group is used in an equimolar amount to the OH-unprotected product, there are mainly obtained the products wherein only the 3-hydroxymethyl moiety is protected. When the reactive derivative of the protecting group is used in an amount of two moles or more to one mole of the OH-unprotected product, there can be obtained the products wherein both the 2- and 3-positions are duly protected.

Moreover, the desired compounds of the present invention are mutually converted, for example, the desired compound [I] having N-oxypyridyl group at the 1-position, can be prepared by subjecting the desired compound [I] having pyridyl group at the 1-position, to oxidation reaction. The desired compound [I-b] having 2(1H)-pyridonyl group at the 1-position, can be prepared by reacting the compound [I] having N-oxypyridyl group at the 1-position, with an acid anhydride, followed by treating the product with a base. The compound [I-e] having N-substituted pyridyl group at the 1-position can be prepared by introducing a corresponding substituent on the N-position of the compound [I] having pyridyl group at the 1-position, by a conventional method.

The starting compound [II] of the present invention is a novel compound, and can be prepared by treating a benzaldehyde compound of the formula [IV]:

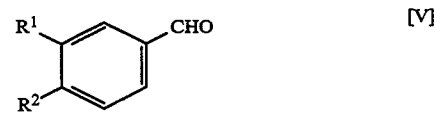

wherein R¹ and R² are the same as defined above, with a halogen (e.g. bromine, etc.), followed by reacting the obtained 6-halogenobenzaldehyde compound with methyl ortho-formate in the presence of an acid catalyst (e.g. strong acidic resin, etc.), and further, by reacting the product with an aldehyde compound of the formula [VI]:

wherein R³ is the same as defined above, in the presence of a basic compound (e.g. n-butyl lithium, etc.) to give a compound of the formula [VII]:

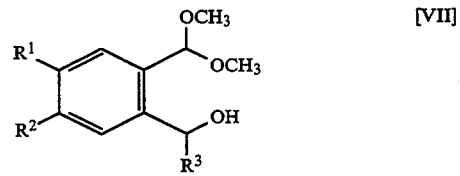

wherein R¹, R² and R³ are the same as defined above, followed by condensing the product with a maleic acid diester, if necessary, by removing the ester residue from the condensation reaction product.

The starting compound [IV] of the present invention is also a novel compound, and can be prepared by reducing a compound of the formula [VIII]:

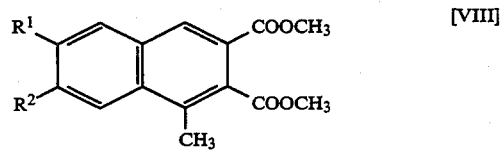

wherein R¹ and R² are the same as defined above, which is prepared according to the process for preparing the starting compound [II], with lithium aluminum hydride, etc., followed by protecting the hydroxy group of the obtained 2,3-bis(hydroxymethyl) compound, oxidizing the 1-methyl group of the product by a conventional method to convert it into an aldehyde group, and reacting the obtained aldehyde compound with a compound of the formula [IX]:

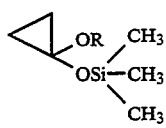

wherein R is the same as defined above, and finally oxidizing the product with an oxidizing agent such as pyridinium chlorochromate, etc.

The starting compounds [II] or [IV] can mutually be converted. The mutual conversion of the starting compounds [II] can be carried out in the same manner as the mutual conversion of the desired compounds [I]. Besides, among the starting compounds [II] and [IV], the compounds, wherein $R^1$ and/or $R^2$ are benzyloxy group, can be converted into the compounds wherein $R^1$ and/or $R^2$ are hydroxy group by a conventional reduction reaction, which are further converted into the compounds wherein $R^1$ and/or $R^2$ are a cyclo-lower alkoxy group or a substituted or unsubstituted lower alkoxy group by protecting said hydroxy groups by a conventional method.

Throughout the present description and the claims, the alkyl group and alkoxy group are ones having 1 to 10 carbon atoms, preferably 1 to 8 carbon atoms, respectively, and the lower alkyl group, the lower alkoxy group and the lower alkylene group are ones having 1 to 6 carbon atoms, preferably 1 to 4 carbon atoms, respectively. The lower alkanoyl group is ones having 2 to 6 carbon atoms, preferably 2 to 5 carbon atoms, and the cyclo-lower alkyl group is ones having 3 to 6 carbon atoms, preferably 5 carbon atoms.

EXAMPLES

The present invention is illustrated in more detail by the following Examples and Reference Examples, but should not be construed to be limited thereto.

Example 1

To tetrahydrofuran (25 ml) is added a 3.4M solution of sodium bis(methoxyethoxy)aluminumhydride in toluene (18.0 ml), and the mixture is cooled to −10° C. To the mixture is added dropwise a suspension of 1-(4-pyridyl)-2,3-bis(methoxycarbonyl)-6,7-diethoxynaphthalene (10.0 g) in tetrahydrofuran (25 ml) over a period of time for 15 minutes. The reaction solution is warmed, and stirred under ice-cooling for 1.5 hour, and thereto is added 15% aqueous sodium hydroxide solution (3.7 ml). To the reaction mixture are added water and methylene chloride, and the insoluble materials are removed by filtration. The filtrate is extracted with methylene chloride, and the extract is washed, dried, and concentrated to give 1-(4-pyridyl)-2,3-bis(hydroxymethyl)-6,7-diethoxynaphthalene (7.89 g).

Yield: 91.1%
M.p. 159°–161° C.

Example 2

A solution of 1-(4-pyridyl)-2,3-bis(methoxycarbonyl)-6,7-dimethoxynaphthalene (2.0 g) in tetrahydrofuran (50 ml) is added dropwise to a suspension of lithium aluminum hydride (100 mg) in tetrahydrofuran (20 ml) at −20° C. The mixture is stirred under ice-cooling for one hour, and thereto are added water (0.1 ml) and 15% aqueous sodium hydroxide solution (0.1 ml). Ten minutes thereafter, water (0.3 ml) is added to the reaction mixture, and the mixture is stirred at room temperature for one hour. The insoluble materials are removed by filtration on celite, and the filtrate is concentrated. The residue is recrystallized from a mixture of ethyl acetate and diethyl ether (1:1) to give 1-(4-pyridyl)-2,3-bis(hydroxymethyl)-6,7-dimethoxynaphthalene (1.35 g).

Yield: 80%
M.p. 118°–120° C.

Example 3

The corresponding dicarboxylic acid methyl ester compounds are treated in the same manner as in Example 2 to give the compounds of Table 1.

TABLE 1

| Ex. No. | $R^1$ | $R^2$ | $R^3$ | Physical Properties |
|---|---|---|---|---|
| 3-(1) | H | H | 4-pyridyl·HCl | M.p. 183–185° C. |
| 3-(2) | $CH_3O$ | $CH_3O$ | 4-pyridyl | M.p. 155–157° C. |
| 3-(3) | $CH_3O$ | $CH_3O$ | 3-pyridyl | M.p. 124–125° C. |
| 3-(4) | $CH_3O$ | $CH_3O$ | 3-fluoro-4-pyridyl | M.p. 173–175° C. |
| 3-(5) | $CH_3CH_2O$ | $CH_3O$ | 4-pyridyl | M.p. 206–208° C. |
| 3-(6) | —O—CH$_2$—O— | | 4-pyridyl | M.p. 208–210° C. |
| 3-(7) | $CH_3O$ | cyclopentyl-O | 4-pyridyl | Powder |

TABLE 1-continued

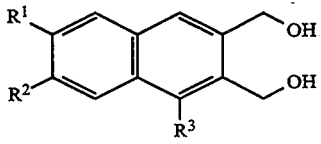

| Ex. No. | R¹ | R² | R³ | Physical Properties |
|---|---|---|---|---|
| 3-(8) | $CH_3CH_2O$ | $CH_3(CH_2)_2O$ | 4-pyridyl | M.p. 131–133° C. |
| 3-(9) | $CH_3CH_2O$ | $CH_3(CH_2)_4O$ | 4-pyridyl | M.p. 101–104° C. |

Example 4

1-(4-Pyridyl)-2,3-bis(hydroxymethyl)-6,7-dimethoxynaphthalene (6.50 g) is dissolved in methylene chloride (50 ml), and thereto are added dropwise acetic anhydride (6.12 g) and triethylamine (6.06 g) under ice-cooling, and the mixture is stirred at room temperature overnight. The mixture is diluted with methylene chloride, and washed with water, dried and concentrated. The resulting residue is recrystallized from a mixture of ethyl acetate and hexane to give 1-(4-pyridyl)-2,3-bis(acetoxymethyl)-6,7-dimethoxynaphthalene (7.45 g).

Yield: 93.6%
M.p. 161°–163° C.

Example 5

The corresponding bis(hydroxymethyl)-type compounds are treated in the same manner as in Example 4 to give the compounds of Table 2.

TABLE 2

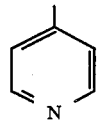

| Ex. No. | R¹ | R² | R³ | Physical properties |
|---|---|---|---|---|
| 5-(1) | $CH_3O$ | $CH_3O$ | 3-pyridyl | M.p. 112–114° C. |
| 5-(2) | $CH_3O$ | $CH_3O$ | 2-pyridyl | Oil |
| 5-(3) | —O—CH₂—O— | | 3-pyridyl | M.p. 130–132° C. |

TABLE 2-continued

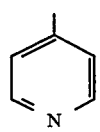

| Ex. No. | R¹ | R² | R³ | Physical properties |
|---|---|---|---|---|
| 5-(4) | $CH_3CH_2O$ | $CH_3O$ | 4-pyridyl | M.p. 145–146° C. |
| 5-(5) | $CH_3CH_2O$ | $CH_3CH_2O$ | 4-pyridyl | M.p. 115–116° C. |

Example 6

To a solution of 1-(4-pyridyl)-2,3-bis(acetoxymethyl)-6,7-dimethoxynaphthalene (5.6 g) in methylene chloride (150 ml) is added m-chloroperbenzoic acid (2.3 g) at room temperature, and the mixture is stirred overnight. The reaction solution is washed successively with aqueous sodium hydrogen carbonate solution and a saturated sodium chloride solution, and dried over magnesium sulfate, and concentrated. The resulting residue is crystallized from diethyl ether to give 1-(N-oxy-4-pyridyl)-2,3-bis(acetoxymethyl)-6,7-dimethoxynaphthalene (4.5 g).

Yield: 78%
M.p. 210°–212° C.

Example 7

The corresponding pyridyl-type compounds are treated in the same manner as in Example 6 to give the compounds of Table 3.

TABLE 3

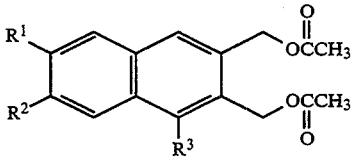

| Ex. No. | R¹ | R² | R³ | Physical properties |
|---|---|---|---|---|
| 7-(1) | $CH_3O$ | $CH_3O$ | 4-pyridyl N→O | Used in the next reaction without purification |
| 7-(2) | $CH_3O$ | $CH_3O$ | 2-pyridyl N→O | M.p. 137–139° C. |

TABLE 3-continued

[Structure: naphthalene with R¹, R² at 6,7 positions, R³ at 1-position, and CH₂OCCH₃(=O) groups at 2,3-positions]

| Ex. No. | R¹ | R² | R³ | Physical properties |
|---|---|---|---|---|
| 7-(3) | —O—CH₂—O— | | [4-pyridyl N→O] | Used in the next reaction without purification |
| 7-(4) | CH₃CH₂O | CH₃O | [4-pyridyl N→O] | Used in the next reaction without purification |
| 7-(5) | CH₃CH₂O | CH₃CH₂O | [4-pyridyl N→O] | M.p. 158–159° C. |

Example 8

To 1-(N-oxy-4-pyridyl)-2,3-bis(acetoxymethyl)-6,7-dimethoynaphthalene (4.5 g) is added acetic anhydride (20 ml), and the mixture is refluxed for 8 hours. The reaction solution is concentrated, and the resulting residue is dissolved in methanol (15 ml), and thereto is added conc. aqueous ammonia solution (0.8 ml) under ice-cooling. The mixture is warmed to room temperature, and stirred for 20 minutes. The precipitated crystals is collected by filtration, and washed with methanol to give 1-(2(1H)-pyridon-4-yl)-2,3-bis(acetoxymethyl)-6,7-dimethoxynaphthalene (1.7 g).

Yield: 76%
M.p. 241°–243° C.

Example 9

(a) 1-(N-Oxy-3-pyridyl)-2,3-bis(acetoxymethyl)-6,7-dimethoxynaphthalene is treated in the same manner as in Example 8, and the resulting product is subjected to silica gel column chromatography (eluent; chloroform:methanol=98:2).

From the fractions eluted first, there is obtained 1-(2(1H)-pyridon-3-yl)-2,3-bis(acetoxymethyl)-6,7-dimethoxynaphthalene.

(b) Further, from the fractions eluted later, there is obtained 1-(2(1H)-pyridon-5-yl)-2,3-bis(acetoxymethyl)-6,7-dimethoxynaphthalene.

Example 10

1-(N-Oxy-3-pyridyl)-2,3-bis(acetoxymethyl)-6,7-methylenedioxynaphthalene is treated in the same manner as in Example 9 to give 1-(2(1H)-pyridon-3-yl)-2,3-bis(acetoxymethyl)-6,7-methylenedioxynaphthalene and 1-(2(1H)-pyridon-5-yl)-2,3-bis(acetoxymethyl)-6,7-methylenedioxynaphthalene.

Example 11

The corresponding N-oxypyridyl-type compounds are treated in the same manner as in Example 8 to give the compounds of Table 4.

TABLE 4

[Structure: naphthalene with R¹, R² at 6,7 positions, R³ at 1-position, and CH₂OCCH₃(=O) groups at 2,3-positions]

| Ex. No. | R¹ | R² | R³ | Physical properties |
|---|---|---|---|---|
| 11-(1) | CH₃O | CH₃O | [4-pyridyl with NH, =O (2-pyridone)] | M.p. 238–240° C. |
| 11-(2) | CH₃CH₂O | CH₃O | [2(1H)-pyridon-4-yl] | M.p. 207–208° C. |
| 11-(3) | CH₃CH₂O | CH₃CH₂O | [2(1H)-pyridon-4-yl] | M.p. 213–214° C. |

Example 12

(a) 1-(2(1H)-Pyridon-4-yl)-2,3-bis(acetoxymethyl)-6,7-dimethoxynaphthalene (1.9 g) is dissolved in dimethylformamide (20 ml), and thereto is added 63% sodium hydride (0.17 g) under ice-cooling. The mixture is stirred at room temperature for 30 minutes, and cooled with ice. To the mixture is added methyl iodide (0.42 ml), and the mixture is stirred at room temperature overnight. The mixture is evaporated to remove the solvent, and to the residue are added ethyl acetate and water, and the mixture is separated. The organic layer is dried, and evaporated to give an oily product (1.0 g).

The resulting oily product is subjected to silica gel column chromatography (eluent; chloroform:acetone=9:1, then, chloroform:methanol=9:1). From the fractions eluted first, there is obtained 1-(2-methoxy-4-pyridyl)-2,3-bis(acetoxymethyl)-6,7-dimethoxynaphthalene.

(b) From the fractions eluted later, there is obtained 1-(N-methyl-2(1H)-pyridon-4-yl)-2,3-bis(acetoxymethyl)-6,7-dimethoxynaphthalene.

Example 13

1-(N-Methyl-2(1H)-pyridon-4-yl)-2,3-bis(acetoxymethyl)-6,7-dimethoxynaphthalene (0.5 g) is dissolved in a 10% solution of ammonia in methanol (20 ml), and the mixture is allowed to stand at room temperature for 2 days. The mixture is evaporated to remove the solvent, and the resulting residue is purified by silica gel column chromatography (eluent; chloroform:methanol=95:5) to give 1-(N-methyl-2(1H)-pyridon-4-yl)-2,3-bis(hydroxymethyl)-6,7-dimethoxynaphthalene (0.25 g).

Yield: 63%

M.p. 176°–178° C. (recrystallized from ethanol)

Example 14

The corresponding pyridone-type compounds and the corresponding alkylating agent are treated in the same manner as in Example 12, and the obtained corresponding N-alkyl-pyridone-type compounds are further treated in the same manner as in Example 13 to give the compounds of Table 5.

TABLE 5

| Ex. No. | $R^1$ | $R^2$ | $R^3$ | Physical properties |
|---|---|---|---|---|
| 14-(1) | $CH_3O$ | $CH_3O$ | pyridon-N-CH$_2$CH$_2$N(CH$_3$)$_2$ | M.p. 140–142° C. |
| 14-(2) | $CH_3O$ | $CH_3O$ | pyridon-N-CH$_2$CH$_2$OH | M.p. 178–180° C. |
| 14-(3) | $CH_3O$ | $CH_3O$ | pyridon-N-CH$_2$C(O)OCH$_2$CH$_3$ | M.p. 158–160° C. |
| 14-(4) | $CH_3O$ | $CH_3O$ | pyridon-N-CH$_2$CH$_2$CH$_2$CH$_3$ | M.p. 159–161° C. |
| 14-(5) | $CH_3O$ | $CH_3O$ | pyridon-N-CH$_2$CH$_2$OCH$_3$ | M.p. 124–126° C. |
| 14-(6) | $CH_3O$ | $CH_3O$ | pyridon-N-CH$_2$CH=CH$_2$ | M.p. 157–159° C. |
| 14-(7) | $CH_3O$ | $CH_3O$ | pyridon-N-CH$_2$CH(CH$_3$)$_2$ | M.p. 188–189° C. |

TABLE 5-continued

Structure: naphthalene with R¹ at 6-position, R² at 7-position, CH₂OH groups at 2,3-positions, and R³ at 1-position.

| Ex. No. | R¹ | R² | R³ | Physical properties |
|---|---|---|---|---|
| 14-(8) | CH₃O | CH₃O | 4-methyl-2-oxo-1(2H)-pyridinyl group with N-CH₂CH₂C(O)NH₂ | M.p. 135-145° C. |
| 14-(9) | CH₃O | CH₃O | 4-methyl-2-oxo-1(2H)-pyridinyl group with N-CH₂-phenyl | M.p. 226-227° C. |
| 14-(10) | CH₃O | CH₃O | 4-methyl-2-oxo-1(2H)-pyridinyl group with N-CH₂CH₂OCH₂CH₂OCH₃ | M.p. 125-126° C. |
| 14-(11) | CH₃O | CH₃O | 4-methyl-2-oxo-1(2H)-pyridinyl group with N-propyl | M.p. 193-194° C. |
| 14-(12) | CH₃O | CH₃O | 4-methyl-2-oxo-1(2H)-pyridinyl group with N-CH₂-(2-furyl) | M.p. 195-196° C. |
| 14-(13) | CH₃O | CH₃O | 4-methyl-2-oxo-1(2H)-pyridinyl group with N-sec-butyl | M.p. 136-137° C. |
| 14-(14) | CH₃O | CH₃O | 4-methyl-2-oxo-1(2H)-pyridinyl group with N-CH₂C(O)CH₃ | M.p. 100-102° C. |
| 14-(15) | CH₃O | CH₃O | 4-methyl-2-oxo-1(2H)-pyridinyl group with N-CH₂CH₂SCH₃ | M.p. 113-115° C. |

TABLE 5-continued

| Ex. No. | R¹ | R² | R³ | Physical properties |
|---|---|---|---|---|
| 14-(16) | CH₃O | CH₃O | pyridon-N-CH₂-(tetrahydrofuran-2-yl) | M.p. 185–187° C. |
| 14-(17) | CH₃O | CH₃O | pyridon-N-CH₂CH₂OCH₂CH₃ | M.p. 191–192° C. |
| 14-(18) | CH₃O | CH₃O | pyridon-N-(CH₂)₇CH₃ | M.p. 110–112° C. |
| 14-(19) | CH₃O | CH₃O | pyridon-N-CH₂-(isoxazol-yl) | M.p. 174–176° C. |

Example 15

(a) 1-(2(1H)-Pyridon-4-yl)-2,3-bis(acetoxymethyl)-6,7-dimethoxynaphthalene and ethyl bromoacetate are treated in the same manner as in Example 12 to give 1-(N-ethoxycarbonylmethyl-2(1H)-pyridon-4-yl)-2,3-bis(acetoxymethyl)-6,7-dimethoxynaphthalene.

(b) To a solution of the above product (2.0 g) in ethanol is added 1N aqueous sodium hydroxide solution at room temperature, and the mixture is stirred for 3 hours. The mixture is evaporated to remove the ethanol, and to the residue is added water, and the mixture is washed with chloroform. The aqueous layer is collected, and the pH value thereof is adjusted with 10% hydrochloric acid to pH 3, and the mixture is concentrated under reduced pressure to give 1-(N-carboxymethyl-2(1H)-pyridon-4-yl)-2,3-bis(hydroxymethyl)-6,7-dimethoxynaphthalene (1.2 g).

Yield: 64%
M.p. >300° C.

The above product is treated with an aqueous sodium hydrogen carbonate solution to give a sodium salt thereof.

Sodium salt: M.p. 170°–195° C. (decomposed)

Further, the above product is treated with conc. aqueous ammonia in methanol to give 1-(N-carbamoylmethyl-2(1H)-pyridon-4-yl)-2,3-bis(hydroxymethyl)-6,7-dimethoxynaphthalene as colorless needles.

M.p. 171°–173° C. (recrystallized from methanol)

Example 16

To a solution of 1-(2(1H)-pyridon-4-yl)-2,3-bis-(acetoxymethyl)-6,7-dimethoxynaphthalene (1.0 g) and acrylonitrile (3 ml) in methanol is added sodium hydroxide (20 mg), and the mixture is heated at 80° C. for 3 minutes. The reaction mixture is concentrated, and subjected to silica gel column chromatography (eluent; chloroform:acetone=10:1, then 5:1), and from the desired fractions, there is obtained 1-[N-(2-cyanoethyl)-2(1H)-pyridon-4-yl]-2,3-bis(acetoxymethyl)-6,7-dimethoxynaphthalene (1.1 g) as pale yellow oil.

Yield: 98%

Example 17

To a solution of 1-[N-(2-cyanoethyl)-2(1H)-pyridon-4-yl]-2,3-bis(acetoxymethyl)-6,7-dimethoxynaphthalene (60 mg) in methanol is added sodium methylate (4 mg) at room temperature. The mixture is stirred for 30 minutes, and thereto is added acetic acid (4 mg), and the mixture is concentrated. The residue is purified by silica gel column chromatography (eluent; chloroform:methanol=10:1 ) to give 1-[N-(2-cyanoethyl)-2(1H)-pyridon-4-yl]-2,3-bis(hydroxymethyl)-6,7-dimethoxynaphthalene (45 mg) as colorless crystal.

Yield: 91%
M.p. 198°–200° C.

Example 18

The corresponding bis(acetoxymethyl)-type compounds are treated in the same manner as in Example 13 to give the compounds of Table 6.

TABLE 6

[Structure: naphthalene with R¹, R² on one ring; CH₂OH groups at 2,3-positions; R³ at position adjacent]

| Ex. No. | R¹ | R² | R³ | Physical properties |
|---|---|---|---|---|
| 18-(1) | CH₃O | CH₃O | 4-methyl-pyridine N-oxide | M.p. 218–220° C. |
| 18-(2) | CH₃O | CH₃O | 3-methyl-pyridine N-oxide | M.p. 153–155° C. |
| 18-(3) | CH₃O | CH₃O | 2-methyl-pyridine N-oxide | M.p. 215–216° C. |
| 18-(4) | CH₃O | CH₃O | 4-methyl-2(1H)-pyridone | M.p. 242–244° C. |
| 18-(5) | CH₃O | CH₃O | 4-methyl-2(1H)-pyridone (isomer) | M.p. 260–261° C. |
| 18-(6) | CH₃O | CH₃O | 3-methyl-2(1H)-pyridone | M.p. 248–250° C. |
| 18-(7) | CH₃O | CH₃O | 6-methyl-2(1H)-pyridone | M.p. 198–200° C. |
| 18-(8) | —O—CH₂—O— | | 3-methyl-2(1H)-pyridone | M.p. >268° C. |

TABLE 6-continued

| Ex. No. | R¹ | R² | R³ | Physical properties |
|---|---|---|---|---|
| 18-(9) | —O—CH₂—O— | | 4-methyl-2(1H)-pyridone | M.p. 168–175° C. |

Example 19

The corresponding pyridone-type compounds are treated with the corresponding alkylating agent in the same manner as in Example 12, and the resulting N-alkylpyridone-type compounds are further treated in the same manner as in Example 13 to give the compounds of Table 7.

TABLE 7

[Structure: naphthalene with R¹, R² on one ring; CH₂OH groups at 2,3-positions; R³ at position adjacent]

| Ex. No. | R¹ | R² | R³ | Physical properties |
|---|---|---|---|---|
| 19-(1) | CH₃O | CH₃O | 3-methyl-1-methyl-2-pyridone | M.p. 200–201° C. |
| 19-(2) | CH₃O | CH₃O | 3-methyl-1-(2-hydroxyethyl)-2-pyridone | Oil |
| 19-(3) | CH₃O | CH₃O | 4-methyl-1-(2-hydroxyethyl)-2-pyridone | M.p. 123–125° C. |
| 19-(4) | CH₃O | CH₃O | 6-methyl-1-methyl-2-pyridone | M.p. 177–178° C. |

Example 20

(a) 1-(2(1H)-Pyridon-5-yl)-2,3-bis(acetoxymethyl)-6,7-dimethoxynaphthalene is treated with methyl iodide in the same manner as in Example 12. The resulting product is subjected to silica gel column chromatography (eluent; chloroform:acetone=9:1, then chloroform:methanol=9:1 ).

(b) From the fractions eluted first, there is obtained 1-(2-methoxy-5-pyridyl)-2,3-bis(acetoxymethyl)-6,7-dimethoxynaphthalene. From the fractions eluted later, there is obtained 1-(N-methyl-2(1H)-pyridon-5-yl)-2,3-bis(acetoxymethyl)-6,7-dimethoxynaphthalene.

Example 21

1-(2-Methoxy-5-pyridyl)-2,3-bis(acetoxymethyl)-6,7-dimethoxynaphthalene is treated in the same manner as in Example 13 to give 1-(2-methoxy-5-pyridyl)-2,3-bis(hydroxymethyl)-6,7-dimethoxynaphthalene.
M.p. 181°–182° C.

Example 22

1-(N-Methyl-2(1H)-pyridon-5-yl)-2,3-bis(acetoxymethyl)-6,7-dimethoxynaphthalene is treated in the same manner as in Example 13 to give 1-(N-methyl-2(1H)-pyridon-5-yl)-2,3bis(hydroxymethyl)-6,7-dimethoxynaphthalene.
M.p. 212°–214° C.

Example 23

The corresponding pyridone-type compounds are treated with the corresponding alkylating agent in the same manner as in Example 20 to give the compound of Table 8.

TABLE 8

| Ex. No. | $R^1$ | $R^2$ | $R^3$ | Physical properties |
|---|---|---|---|---|
| 23-(1)-(a) | $CH_3O$ | $CH_3O$ | pyridyl-O-CH$_2$CH$_2$OH | Used in the next reaction without purification |
| 23-(1)-(b) | $CH_3O$ | $CH_3O$ | N-(CH$_2$CH$_2$OH)-pyridon | Used in the next reaction without purification |
| 23-(2)-(a) | $CH_3O$ | $CH_3O$ | pyridyl-O-CH$_2$CH$_2$N(CH$_3$)$_2$ | Used in the next reaction without purification |
| 23-(2)-(b) | $CH_3O$ | $CH_3O$ | N-(CH$_2$CH$_2$N(CH$_3$)$_2$)-pyridon | Used in the next reaction without purification |

Example 24

The corresponding bis(acetoxymethyl)-type compounds are treated in the same manner as in Example 13 to give the compounds of Table 9.

TABLE 9

| Ex. No. | $R^1$ | $R^2$ | $R^3$ | Physical properties |
|---|---|---|---|---|
| 24-(1) | $CH_3O$ | $CH_3O$ | pyridyl-O-CH$_2$CH$_2$OH | M.p. 156–158° C. |

TABLE 9-continued

Structure: naphthalene with R¹, R² at 6,7 positions, R³ at position 1, and two CH₂OH groups at 2,3 positions.

| Ex. No. | R¹ | R² | R³ | Physical properties |
|---|---|---|---|---|
| 24-(2) | CH₃O | CH₃O | 1-(2-hydroxyethyl)-6-methyl-2(1H)-pyridon-4-yl | M.p. 90–92° C. |
| 24-(3) | CH₃O | CH₃O | 2-(2-dimethylaminoethoxy)-6-methylpyridin-4-yl | Oil |
| 24-(4) | CH₃O | CH₃O | 1-(2-dimethylaminoethyl)-6-methyl-2(1H)-pyridon-4-yl | Oil |

Example 25

To a solution of 1-(N-butyl-2(1H)-pyridon-4-yl)-2,3-bis(methoxycarbonyl)-6,7-dimethoxynaphthalene (226 mg) in tetrahydrofuran (2 ml) is added sodium borohydride (100 mg), and the mixture is refluxed. To the reaction solution is added dropwise methanol (0.4 ml) over a period of time for 20 minutes. One hour thereafter, the reaction solution is allowed to cool, and neutralized with 10% hydrochloric acid. The mixture is extracted with chloroform, and the chloroform layer is washed with water, dried and concentrated. The resulting residue is subjected to silica gel column chromatography (eluent; chloroform:methanol=20:1), and the desired fractions are concentrated to give 1-(N-butyl-2(1H)-pyridon-4-yl)-2,3-bis(hydroxymethyl)-6,7-dimethoxynaphthalene (165 mg) as crystal.

Yield: 83%

M.p. 159°–161° C.

Example 26

The corresponding dicarboxylic acid ester-type starting compounds are treated in the same manner as in Example 25 to give the compounds of Table 10.

TABLE 10

Structure: naphthalene with R¹, R² at 6,7 positions, R³ at position 1, and two CH₂OH groups at 2,3 positions.

| Ex. No. | R¹ | R² | R³ | Physical properties |
|---|---|---|---|---|
| 26-(1) | CH₃O | CH₃CH₂O | 1-butyl-2(1H)-pyridon-4-yl | M.p. 164–166° C. |
| 26-(2) | CH₃O | CH₃CH₂O | 1-(2-methoxyethyl)-2(1H)-pyridon-4-yl | M.p. 168–170° C. |
| 26-(3) | CH₃O | HOCH₂CH₂O | 1-(2-methoxyethyl)-2(1H)-pyridon-4-yl | M.p. 154–155° C. |

TABLE 10-continued

[Naphthalene structure with R¹, R² at 6,7-positions; R³ at 1-position; CH₂OH groups at 2,3-positions]

| Ex. No. | R¹ | R² | R³ | Physical properties |
|---|---|---|---|---|
| 26-(4) | CH₃O | CH₃O—CH₂CH₂O | 4-methyl-1-(methoxymethyl)-2-pyridon-3-yl | M.p. 170–172° C. |
| 26-(5) | CH₃O | CH₃OCH₂—CH₂OCH₂O | 4-methyl-1-(methoxymethyl)-2-pyridon-3-yl | M.P. 108–109° C. |
| 26-(6) | CH₃O | PhCH₂O | 4-methyl-1-(methoxymethyl)-2-pyridon-3-yl | M.p. 143–144° C. |
| 26-(7) | CH₃CH₂O | CH₃O | 4-methyl-2-pyridon-3-yl (NH) | M.p. 158–159° C. |
| 26-(8) | CH₃CH₂O | CH₃O | 4-methyl-1-propyl-2-pyridon-3-yl | M.p. 173–175° C. |
| 26-(9) | CH₃CH₂O | CH₃O | 4-methyl-1-(methoxyethyl)-2-pyridon-3-yl | M.p. 162–164° C. |
| 26-(10) | CH₃CH₂O | CH₃O | 4-methyl-1-(methoxymethyl)-2-pyridon-3-yl | M.p. 159–160° C. |
| 26-(11) | CH₃CH₂O | CH₃O | 4-methyl-1-[(2-methoxyethoxy)methyl]-2-pyridon-3-yl | M.p. 93–94° C. |

TABLE 10-continued

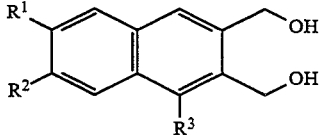

| Ex. No. | R¹ | R² | R³ | Physical properties |
|---|---|---|---|---|
| 26-(12) | CH₃CH₂O | CH₃CH₂O | 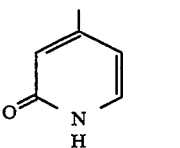 | M.p. 247–248° C. |
| 26-(13) | CH₃CH₂O | CH₃CH₂O | 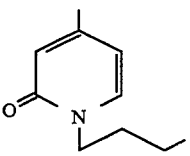 | M.p. 149–150° C. |
| 26-(14) | CH₃CH₂O | CH₃CH₂O | 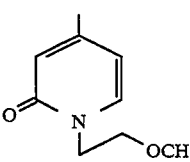 | M.p. 126–127° C. |
| 26-(15) | HOCH₂CH₂O | CH₃O | 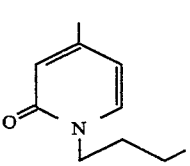 | M.p. 162–164° C. |
| 26-(16) | HOCH₂CH₂O | CH₃O | 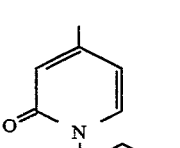 | M.p. 169–171° C. |
| 26-(17) | HOCH₂CH₂O | CH₃O | 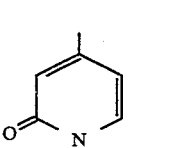 | M.p. 133–135° C. |

Example 27

(a) To a suspension of 1-(4-pyridyl)-2,3-bis(hydroxymethyl)-6,7-diethoxynaphthalene (7.0 g) in dry dimethylformamide (14 ml) is added 2-methoxyethyl iodide (7.35 g), and the mixture is stirred at 80° C. overnight. The mixture is allowed to cool, and thereto added ethyl acetate. The precipitated crystal is collected by filtration to give 4-[2,3-bis(hydroxymethyl)-6,7-diethoxy-1naphthyl]-N-(2-methoxyethyl)pyridinium iodide (8.50 g).

Yield: 79.8%

M.p. 174°–176°C. (recrystallized from acetone)

(b) To a mixture of the above product (2.0 g) in water (5 ml) and methanol (10 ml) are simultaneously added dropwise a solution of potassium ferricyanide (4.8 g) in water (10 ml) and 2N aqueous sodium hydroxide solution (15.2 ml) with stirring at 10° C. over a period of time for one hour. The mixture is warmed to room temperature, and stirred for 5 hours. The mixture is evaporated to remove the methanol, and the residue is extracted with methylene chloride. The extract is washed, dried, and concentrated. The resulting residue is crystallized from ethyl acetate to give 1-[N(-2-methoxyethyl)-2(1H)-pyridon-4-yl]-2,3-bis(hydroxymethyl)- 6,7-diethoxynaphthalene (1.82 g).

Yield: 60.1%

M.p. 126°–127° C.

Example 28

The corresponding compounds are treated in the same manner as in Example 27 to give the compounds of Table 11.

TABLE 11

[Structure: naphthalene with R¹ at position 6, R² at position 7, two CH₂OH groups at positions 2,3, and R³ at position 1]

| Ex. No. | R¹ | R² | R³ | Physical properties |
|---|---|---|---|---|
| 28-(1) | CH₃O | (CH₃)₂CHO | 4-methyl-1-(2-methoxyethyl)-2-oxo-1,2-dihydropyridin-yl | M.p. 184–185° C. |
| 28-(2) | CH₃O | cyclopentyl-O | 4-methyl-1-(2-methoxyethyl)-2-oxo-1,2-dihydropyridin-yl | M.p. 216–217° C. |
| 28-(3) | CH₃CH₂O | CH₃O | 4-methyl-1-(2-methoxyethyl)-2-oxo-1,2-dihydropyridin-yl | M.p. 162–164° C. |
| 28-(4) | CH₃CH₂O | CH₃(CH₂)₂O | 4-methyl-1-(2-methoxyethyl)-2-oxo-1,2-dihydropyridin-yl | M.p. 119–121° C. |
| 28-(5) | CH₃CH₂O | CH₃(CH₂)₄O | 4-methyl-1-(2-methoxyethyl)-2-oxo-1,2-dihydropyridin-yl | M.p. 118–120° C. |

Example 29

To a solution of 1-(1-oxo-3-ethoxycarbonylpropyl)-2,3-bis(acetoxymethyl)-6,7-dimethoxynaphthalene (340 mg) in ethanol (40 ml) is added hydrazine hydrate (1 ml), and the mixture is refluxed overnight. The reaction solution is allowed to cool, and concentrated. To the resulting residue is added water, and the mixture is extracted with chloroform. The chloroform layer is washed with water, dried, and concentrated to give 1-(4,5-dihydro-3(2H)-pyridadinon-6-yl)-2,3-bis(hydroxymethyl)-6,7-dimethoxynaphthalene (170 mg) as crystal.

Yield: 67%

M.p. 210°–212° C.

Example 30

(a) To a solution of 1-(4,5-dihydro-3(2H)-pyridadinon-6-yl)-2,3-bis(hydroxymethyl)-6,7-dimethoxynaphthalene (344 mg) in methylene chloride (10 ml) are added triethylamine (1.24 ml) and dimethylaminopyridine (20 mg). To the mixture is added acetic anhydride (896 mg) at room temperature, and the mixture is stirred for 4 days. The reaction solution is washed with water, dried over magnesium sulfate and concentrated. The resulting residue is purified by silica gel column chromatography (eluent; chloroform:acetone=5:1). The desired fractions are concentrated, and the residue is crystallized from diethyl ether to give 1-(4,5-dihydro-3(2H)-pyridadinon-6-yl)-2,3-bis(acetoxymethyl)-6,7-dimethoxynaphthalene (255 mg).

Yield: 60%

M.p. 184°–186° C.

(b) To a solution of the above product (200 mg) in dioxane (5 ml) is added dicyanodichloroquinone (427 mg), and the mixture is refluxed for 2 hours. The mixture is allowed to cool, and concentrated, and chloroform is added to the resulting residue. The insoluble materials are removed by filtration, and the filtrate is washed with water, dried, and concentrated. The resulting residue is purified by silica gel column chromatography (eluent; chloroform:acetone=5:1), and the desired fractions are concentrated to give 1-(3(2H)-pyridadinon-6-yl)-2,3-bis(acetoxymethyl)-6,7-dimethoxynaphthalene (150 mg) as an oily product.

Yield: 75%

(c) To a solution of the above product (100 mg) in methanol (5 ml) is added sodium methylate (30 mg) at room temperature. After stirring for one hour, to the mixture is added acetic acid (34 mg), and the mixture is concentrated. The residue is purified by silica gel column chromatography (eluent; chloroform:methanol=10:1), and the desired fractions are concentrated. The residue is crystallized from diethyl ether to give 1-(3(2H)-pyridadinon-6-yl)-2,3-bis(hydroxymethyl)-6,7-dimethoxynaphthalene (40 mg).

Yield: 51%
M.p. 228°–229° C.

Example 31

To a solution of 1-(N-butyl-2(1H)-pyridon-4-yl)-2,3-bis(hydroxymethyl)-6,7-dimethoxynaphthalene (1.5 g) in methylene chloride (10 ml) are added successively triethylamine (1.3 ml), dimethylaminopyridine (300 mg) and acetic anhydride (853 mg) at room temperature. After stirring at room temperature overnight, the reaction solution is washed with water, and the methylene chloride layer is dried and concentrated. The residue is purified by silica gel column chromatography (eluent; chloroform:methanol=20:1), and the desired fractions are concentrated. The precipitated crystal is collected by filtration to give 1-(N-butyl-2(1H)-pyridon-4-yl)-2,3-bis(acetoxymethyl)-6,7-dimethoxynaphthalene (1.40 g).

Yield: 77%
M.p. 134°–135° C.

Example 32

To a suspension of 1-[N-(2-methoxyethyl)-2(1H)-pyridon-4-yl]-2,3-bis(hydroxymethyl)-6-ethoxy-7-methoxynaphthalene in pyridine is added pivaloyl chloride (2.86 ml) under ice-cooling. The mixture is warmed to room temperature, and stirred overnight. The mixture is evaporated to remove the pyridine, and to the residue are added water and ethyl acetate, and separated. The ethyl acetate layer is washed, dried, and concentrated, and the resulting residue is subjected to silica gel column chromatography (eluent; chloroform:acetone=5:1, then chloroform:methanol=20:1). The desired fractions are concentrated, and the resulting residue is crystallized from diethyl ether to give 1-[N-(2-methoxyethyl)-2(1H)-pyridon-4-yl]-2-hydroxymethyl-3-pivaloyloxymethyl-6-ethoxy-7-methoxynaphthalene (5.3 g).

Yield: 55%
M.p. 134°–135° C.

Example 33

To a suspension of sodium hydride in hexamethylphosphoric triamide (40 ml) is added a solution of 1-(3-pyridyl)-2,3-bis(hydroxymethyl)-6,7-dimethoxynaphthalene in hexamethylphosphoramide (10 ml) under ice-cooling. The mixture is warmed to room temperature, and then stirred for 30 minutes. To the reaction solution is added neo-pentyl tosylate (3.67 g), and the mixture is reacted at 100° C. for 30 minutes. The mixture is allowed to cool, and thereto is added water, and the mixture is extracted with ethyl acetate. The extract is washed with water, dried, and concentrated. The resulting residue is subjected to silica gel column chromatography (eluent; chloroform:acetone=5:1), and the desired fractions are concentrated to give 1-(3-pyridyl)-2-hydroxymethyl-3-neo-pentyloxymethyl-6,7-dimethoxynaphthalene (1.5 g) as an oily product.

A solution of the above product in chloroform is treated with a solution of hydrogen chloride in methanol to give a hydrochloride of the above product.

Hydrochloride: M.p. 135°–145° C. (recrystallized from diethyl ether)

Reference Example 1

(a) 3,4-Dimethoxybenzaldehyde (398.8 g) is dissolved in acetic acid (1.8 liter), and thereto is added dropwise bromine (136 ml) at room temperature over a period of time for 4 hours. After stirring overnight, to the mixture is added dropwise bromine (60 ml) gradually, and the mixture is stirred overnight. To the reaction solution is added water (7 liters), and the precipitated crystal is collected by filtration, washed with water to give a crystalline product, which is dissolved in chloroform (2 liters). The mixture is washed successively with water, aqueous sodium thiosulfate solution and a saturated sodium chloride solution. The chloroform layer is dried and concentrated, and crystallized from diisopropyl ether to give 6-bromo-3,4-dimethoxygbenzaldehyde (470 g) as colorless crystal.

Yield: 79.9%
M.p. 144°–146° C.

(b) 6-Bromo-3,4-dimethoxybenzaldehyde (470 g) is suspended in methanol (600 ml), and thereto are added methyl ortho-formate (1025 ml) and IRA-120 (H+-type) (10 g), and the mixture is refluxed for one hour. The mixture is cooled to room temperature, and the insoluble materials are removed by filtration. The filtrate is concentrated under reduced pressure, and the resulting residue is dissolved in diethyl ether. The mixture is washed, dried, and evaporated to remove the diethyl ether. The resulting residue is distilled under reduced pressure to give 6-bromo-3,4-dimethoxybenzaldehyde dimethylacetal (522 g) as main distillate (133°–138° C./1Torr).

Yield: 93.9%

Reference Example 2

The corresponding aldehyde-type starting compounds are treated in the same manner as in Reference Example 1 to give the compounds of Table 12.

TABLE 12

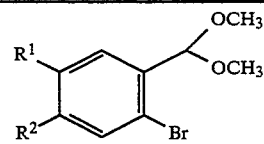

| Ref. Ex. No. | $R^1$ | $R^2$ | Physical properties |
|---|---|---|---|
| 2-(1) | H | H | Oil |
| 2-(2) | $CH_3O$ | $CH_3O$ | b.p. 133–138° C./ 1 Torr |
| 2-(3) | $CH_3CH_2O$ | $CH_3O$ | b.p. 170–175° C./ 3 Torr |
| 2-(4) | $CH_3O$ | $CH_3CH_2O$ | b.p. 160–162° C./ 2 Torr |
| 2-(5) | —O—$CH_2$—O— | | Oil |
| 2-(6) | $CH_3CH_2O$ | $CH_3CH_2O$ | b.p. 145–150° C./ 1 Torr |

TABLE 12-continued $R^1$, $R^2$ substituted benzene with $-CH(OCH_3)_2$ and $Br$ groups

| Ref. Ex. No. | $R^1$ | $R^2$ | Physical properties |
|---|---|---|---|
| 2-(7) | $CH_3O$ | benzyloxy ($-OCH_2C_6H_5$) | Oil |
| 2-(8) | benzyloxy ($-OCH_2C_6H_5$) | $CH_3O$ | Oil |
| 2-(9) | $CH_3CH_2O$ | $CH_3(CH_2)_2O$ | Oil |
| 2-(10) | $CH_3CH_2O$ | $CH_3(CH_2)_4O$ | Oil |
| 2-(11) | $CH_3O$ | cyclopentyloxy | b.p. 150–155° C./1 Torr |

Reference Example 3

A solution of 6-bromo-3,4-dimethoxybenzaldehyde dimethylacetal compound (20 g) in tetrahydrofuran (100 ml) is cooled to −60° C., and thereto is added dropwise a solution of n-butyl lithium in hexane (1.6M, 45.1 ml) over a period of time for 20 minutes under nitrogen atmosphere. The reaction solution is reacted at the same temperature for 30 minutes, and thereto is added dropwise a solution of isonicotinic aldehyde (7.36 g) in tetrahydrofuran (50 ml) over a period of time for 20 minutes. After reacting for one hour, to the reaction solution are added water and ethyl acetate (200 ml), and the mixture is separated. The ethyl acetate layer is washed with a saturated sodium chloride solution, dried over magnesium sulfate, and evaporated to remove the ethyl acetate to give 3,4-dimethoxy-6-(4-pyridyl)-hydroxymethylbenzaldehyde dimethylacetal (15.4 g).

Yield: 70%

M.p. 120°–125° C.

Reference Example 4

The corresponding compounds are treated in the same manner as in Reference Example 3 to give the compounds of Table 13.

TABLE 13

$R^1$, $R^2$ substituted benzene with $-CH(OCH_3)_2$ and $-CH(OH)R^3$ groups

| Ref. Ex. No. | $R^1$ | $R^2$ | $R^3$ | Physical properties |
|---|---|---|---|---|
| 4-(1) | H | H | 4-pyridyl | Oil |
| 4-(2) | $CH_3O$ | $CH_3O$ | 4-pyridyl | Oil |
| 4-(3) | $CH_3O$ | $CH_3O$ | 3-pyridyl | Oil |
| 4-(4) | $CH_3O$ | $CH_3O$ | 2-pyridyl | Oil |
| 4-(5) | $CH_3O$ | $CH_3O$ | $CH_3$ | Oil |
| 4-(6) | $CH_3CH_2O$ | $CH_3O$ | 4-pyridyl | M.p. 114–115° C. |

TABLE 13-continued $$R^1, R^2 \text{-substituted benzene with } CH(OCH_3)_2 \text{ and } CH(OH)R^3 \text{ groups}$$

| Ref. Ex. No. | $R^1$ | $R^2$ | $R^3$ | Physical properties |
|---|---|---|---|---|
| 4-(7) | $CH_3O$ | $CH_3CH_2O$ | 4-pyridyl | M.p. 116–118° C. |
| 4-(8) | —O—CH$_2$—O— | | 3-pyridyl | Oil |
| 4-(9) | $CH_3CH_2O$ | $CH_3CH_2O$ | 4-pyridyl | M.p. 108–109° C. |
| 4-(10) | $CH_3O$ | phenyl-$CH_2O$ | 4-pyridyl | Oil |
| 4-(11) | phenyl-$CH_2O$ | $CH_3O$ | 4-pyridyl | Oil |
| 4-(12) | $CH_3CH_2O$ | $CH_3(CH_2)_2O$ | 4-pyridyl | M.p. 110–112° C. |
| 4-(13) | $CH_3CH_2O$ | $CH_3(CH_2)_4O$ | 4-pyridyl | M.p. 106–109° C. |
| 4-(14) | $CH_3O$ | cyclopentyl-O | 4-pyridyl | Oil |

Reference Example 5

3,4-Dimethoxy-6-(4-pyridyl)hydroxymethylbenzaldehyde dimethylacetal (15 g) is refluxed for 3 hours in a mixture of methanol (200 ml) and acetic acid (30 ml). The mixture is evaporated to about ¼ volume, and separated with a mixture of chloroform and aqueous sodium hydrogen carbonate solution. The organic layer is collected, dried, and concentrated to give 1-methoxy-3-(4-pyridyl)-5,6-dimethoxyphthalane (13.1 g) as an oil, which is used in the subsequent reaction without purification.

Yield: 94%

Reference Example 6

To a solution of lithium diisopropylamide (18.4 g) in tetrahydrofuran (300 ml) is added dropwise a solution of 1-methoxy-3-(4-pyridyl)-5,6-dimethoxyphthalane (13.1 g) in tetrahydrofuran (100 ml) at −70° C., and the mixture is stirred. To the mixture are successively added dropwise acetic acid (10.9 g) and dimethyl maleate (13.1 g), and the mixture is stirred at room temperature overnight. The reaction mixture is separated with ethyl acetate and aqueous sodium hydrogen carbonate solution. The organic layer is collected, washed with water, dried, and concentrated. The residue is subjected to silica gel column chromatography (eluent; n-hexane:ethyl acetate=1:1) to give 1-(4-pyridyl)-2,3-bis(methoxycarbonyl)-6,7-dimethoxy-1,4-epoxy-1,4-dihydronaphthalene (3.5 g).

Reference Example 7

1-(4-Pyridyl)- 2,3-bis(methoxycarbonyl)-6,7-dimethoxy-1,4-epoxy-1,4-dihydronaphthalene (3.0 g) and trifluoroborane.diethyl ether (1.95 g) are added to acetonitrile (100 ml), and the mixture is refluxed for 2 hours. The reaction solution is separated with a mixture of chloroform (300 ml) and aqueous sodium hydrogen carbonate solution (50 ml), and the organic layer is further washed with aqueous sodium hydrogen carbonate solution, dried, and concentrated. The resulting residue is washed with a small amount of diethyl ether to give 1-(4-pyridyl)-2,3-bis(methoxy-carbonyl)-6,7-dimethoxynaphthalene (2.1 g) as crystal.
Yield: 73%
M.p. 196°–198° C.

Reference Example 8

To a solution of 3,4-dimethoxy-6-(4-pyridyl) hydroxymethylbenzaldehyde dimethylacetal (18.4 g) in a mixture of acetic acid (50 ml) and toluene (50 ml) is added dimethyl maleate (8.64 ml), and the mixture is refluxed for one hour. To the mixture is added methanesulfonic acid (9.33 ml), and the mixture is refluxed for 8 hours while removing the resulting water with a Dean-Stalk apparatus. The mixture is cooled to room temperature, and concentrated. The residue is dissolved in chloroform, and the pH value thereof is adjusted with aqueous potassium carbonate solution to pH 8. The mixture is extracted twice with each 100 ml of chloroform, and the extracts are washed with a saturated sodium chloride solution, dried over magnesium sulfate, and concentrated. The resulting residue is crystallized from diethyl ether to give a diester compound, 1-(4-pyridyl)-2,3-bis(methoxycarbonyl)-6,7-dimethoxynaphthalene (13.5 g).
Yield: 62.2%
M.p. 196°–198° C.

Reference Example 9

1-(4-Pyridyl)-2,3-bis(methoxycarbonyl)-6-benzyloxy-7-methoxynaphthalene (2.3 g) is dissolved in acetic acid (50 ml), and thereto is added 10% palladium-carbon. The mixture is subjected to hydrogenation for 3 hours with shaking by using a moderate-pressure reduction apparatus (Parr). The palladium-carbon is removed by filtration, and the filtrate is concentrated. The precipitated crystal is washed with diethyl ether to give 1-(4-pyridyl)-2,3-bis(methoxycarbonyl)-6-hydroxy-7-methoxynaphthalene (1.8 g).
Yield: 98%
M.p. 210°–212° C.

Reference Example 10

To a solution of 1-(4-pyridyl)-2,3-bis(methoxycarbonyl)-6-hydroxy-7-methoxynaphthalene (17 g) in dimethylformamide (50 ml) is added gradually sodium hydride (60% dispersion-type) under ice-cooling, and the mixture is stirred at room temperature for 30 minutes. The mixture is cooled with ice, and thereto is added 2-methoxyethyl iodide (10.3 g). The mixture is stirred at room temperature for 2 hours, and heated to 80° C. One hour thereafter, the reaction solution is allowed to cool, and concentrated. The resulting residue is dissolved in ethyl acetate, washed with water, dried, and concentrated. The precipitated crystal is washed with diethyl ether to give 1-(4-pyridyl)-2,3-bis(-methoxycarbonyl)-6-(2-methoxyethyloxy)-7-methoxynaphthalene (8.5 g).
Yield: 43%
M.p. 156°–158° C.

Reference Example 11

The corresponding compounds are treated in the same manner as in Reference Examples 1 to 8, and the obtained products are further treated in the same manner as in Reference Examples 9, 10, if necessary, to give the dicarboxylic acid ester-type compounds of Table 14.

TABLE 14

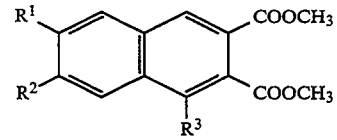

| Ref. Ex. No. | $R^1$ | $R^2$ | $R^3$ | Physical properties |
| --- | --- | --- | --- | --- |
| 11-(1) | H | H | 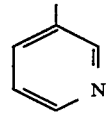 | Oil |
| 11-(2) | $CH_3O$ | $CH_3O$ | 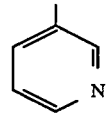 | Oil |

TABLE 14-continued
| Ref. Ex. No. | R¹ | R² | R³ | Physical properties |
|---|---|---|---|---|
| 11-(3) | CH₃O | CH₃O | 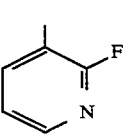 | M.p. 163–165° C. |
| 11-(4) | CH₃O | CH₃O | CH₃ | M.p. 142–144° C. |
| 11-(5) | CH₃O | CH₃O | 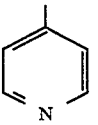 | Powder |
| 11-(6) | CH₃CH₂O | CH₃O | 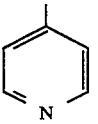 | M.p. 186–187° C. |
| 11-(7) | CH₃O | CH₃CH₂O | 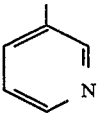 | M.p. 179–181° C. |
| 11-(8) | —O—CH₂—O— | | 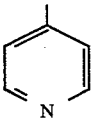 | M.p. 156–157° C. |
| 11-(9) | CH₃CH₂O | CH₃CH₂O | 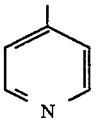 | M.p. 149–150° C. |
| 11-(10) | CH₃O | 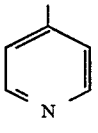 | 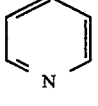 | M.p. 202–203° C. |
| 11-(11) | CH₃O | HO |  | M.p. 261–262° C. |
| 11-(12) |  | CH₃O |  | M.p. 236–238° C. |

TABLE 14-continued $R^1, R^2$ substituted naphthalene-2,3-dicarboxylic acid dimethyl ester with $R^3$ at position 1:

| Ref. Ex. No. | $R^1$ | $R^2$ | $R^3$ | Physical properties |
|---|---|---|---|---|
| 11-(13) | HO | CH$_3$O | 4-pyridyl | M.p. 210–212° C. |
| 11-(14) | CH$_3$CH$_2$O | CH$_3$(CH$_2$)$_2$O | 4-pyridyl | M.p. 159–161° C. |
| 11-(15) | CH$_3$CH$_2$O | CH$_3$(CH$_2$)$_4$O | 4-pyridyl | M.p. 147–149° C. |
| 11-(16) | CH$_3$O | CH$_3$O—C(=O)—CH$_2$O | 4-pyridyl | M.p. 176–178° C. |
| 11-(17) | CH$_3$O | CH$_3$OCH$_2$CH$_2$O | 4-pyridyl | M.p. 156–157° C. |
| 11-(18) | CH$_3$O | CH$_3$OCH$_2$CH$_2$OCH$_2$O | 4-pyridyl | M.p. 90–92° C. |
| 11-(19) | CH$_3$O | cyclopentyl-O | 4-pyridyl | M.p. 150–152° C. |
| 11-(20) | CH$_3$O—C(=O)—CH$_2$O | CH$_3$O | 4-pyridyl | M.p. 214–215° C. |
| 11-(21) | CH$_3$OCH$_2$CH$_2$O | CH$_3$O | 4-pyridyl | M.p. 156–158° C. |

Reference Example 12

To a solution of 1-(4-pyridyl)-2,3-bis(methoxycarbonyl)-6,7-dimethoxynaphthalene (5 g) in methylene chloride (300 ml) is added m-chloroperbenzoic acid (8.1 g) under ice-cooling, and the mixture is warmed to room temperature, and stirred overnight. The reaction solution is washed successively with 10% aqueous sodium hydrogensulfite solution, aqueous potassium carbonate solution and saturated sodium chloride solution.

The mixture is dried, and concentrated to give 1-(N-oxy-4-pyridyl)-2,3-bis(methoxycarbonyl)-6,7-dimethoxynaphthalene (15.0 g) as crystal.

Yield: 96%

M.p. 224°–226° C.

Reference Example 13

The corresponding pyridine-type starting compounds are treated in the same manner as in Reference Example 12 to give the compounds of Table 15.

TABLE 15

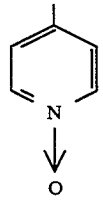

| Ref. Ex. No. | R¹ | R² | R³ | Physical properties |
|---|---|---|---|---|
| 13-(1) | $CH_3CH_2O$ | $CH_3O$ | 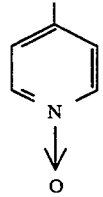 | M.p. 190–197° C. |
| 13-(2) | $CH_3O$ | $CH_3CH_2O$ | 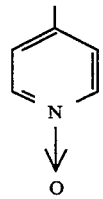 | M.p. 220–230° C. |
| 13-(3) | $CH_3CH_2O$ | $CH_3CH_2O$ | 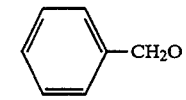 | M.p. 177–178° C. |
| 13-(4) | $CH_3O$ | 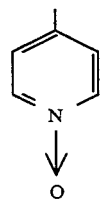 | 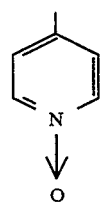 | Used in the next reaction without purification |
| 13-(5) | $CH_3O$ | $CH_3OCH_2CH_2O$ | 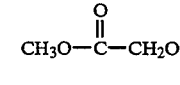 | M.p. 188–189° C. |
| 13-(6) | $CH_3O$ | $CH_3O-\overset{O}{\underset{}{C}}-CH_2O$ | 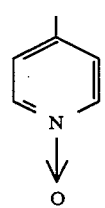 | Used in the next reaction without purification |

TABLE 15-continued

[Structure: naphthalene with R¹, R² at 6,7 positions, COOCH₃ at 2,3 positions, R³ at 1 position]

| Ref. Ex. No. | R¹ | R² | R³ | Physical properties |
|---|---|---|---|---|
| 13-(7) | CH₃O—C(=O)—CH₂O | CH₃O | 4-(N-oxy-pyridyl) | M.p. 227–228° C. |
| 13-(8) | CH₃OCH₂CH₂O | CH₃O | 4-(N-oxy-pyridyl) | M.p. 161–163° C. |
| 13-(9) | CH₃O | CH₃OCH₂CH₂—OC₂H₅ | 4-(N-oxy-pyridyl) | — |

Reference Example 14

To a solution of 1-(N-oxy-4-pyridyl)-2,3-bis(methoxycarbonyl)-6,7-dimethoxynaphthalene (10 g) in dimethylformamide (75 ml) ia added acetic anhydride (24 ml), and the mixture is stirred at 150° C. for 8 hours. The reaction solution is allowed to cool, and concentrated. The resulting residue is dissolved in methanol (20 ml), and thereto is added saturated aqueous ammonia (10 ml) at room temperature, and the mixture is stirred for 30 minutes. The precipitated crystal is collected by filtration to give 1-(2(1H)-pyridon-4-yl)-2,3-bis(methoxycarbonyl)-6,7-dimethoxynaphthalene (8.6 g).

Yield: 86%
M.p. >250° C.

Reference Example 15

The corresponding N-oxypyridine-type starting compounds are treated in the same manner as in Reference Example 14 to give the pyridone-type compounds of Table 16.

TABLE 16

[Structure: naphthalene with R¹, R² at 6,7 positions, COOCH₃ at 2,3 positions, R³ at 1 position]

| Ref. Ex. No. | R¹ | R² | R³ | Physical properties |
|---|---|---|---|---|
| 16-(1) | CH₃O | CH₃O | 2(1H)-pyridon-4-yl | M.p. >250° C. |

TABLE 16-continued $$\begin{array}{c} R^1 \diagup\diagdown\diagup\diagdown COOCH_3 \\ R^2 \diagdown\diagup\diagdown\diagup \\ R^3 \end{array}$$

COOCH₃ (top), COOCH₃ (bottom)

| Ref. Ex. No. | R¹ | R² | R³ | Physical properties |
|---|---|---|---|---|
| 16-(2) | CH₃CH₂O | CH₃O | 2-oxo-1,2-dihydropyridin-4-yl | M.p. >235° C. |
| 16-(3) | CH₃O | CH₃CH₂O | 2-oxo-1,2-dihydropyridin-4-yl | M.p. 225–228° C. |
| 16-(4) | CH₃CH₂O | CH₃CH₂O | 2-oxo-1,2-dihydropyridin-4-yl | M.p. 234–235° C. |
| 16-(5) | CH₃O | C₆H₅CH₂O | 2-oxo-1,2-dihydropyridin-4-yl | M.p. 251–252° C. |
| 16-(6) | CH₃O | CH₃O−C(=O)−CH₂O | 2-oxo-1,2-dihydropyridin-4-yl | M.p. 148–149° C. |
| 16-(7) | CH₃O | CH₃OCH₂CH₂O | 2-oxo-1,2-dihydropyridin-4-yl | Oil |
| 16-(8) | CH₃O−C(=O)−CH₂O | CH₃O | 2-oxo-1,2-dihydropyridin-4-yl | M.p. 225–228° C. |
| 16-(9) | CH₃OCH₂CH₂O | CH₃O | 2-oxo-1,2-dihydropyridin-4-yl | M.p. 207–206° C. |

TABLE 16-continued

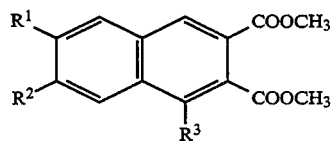

| Ref. Ex. No. | $R^1$ | $R^2$ | $R^3$ | Physical properties |
|---|---|---|---|---|
| 16-(10) | $CH_3O$ | $CH_3OCH_2CH_2-$ $OCH_2O$ | ![4-(2-pyridon-1H)yl] | Used in the next reaction without purification |

Reference Example 16

To a solution of 1-(2(1H)-pyridon-4-yl)-2,3-bis(methoxycarbonyl)-6,7-dimethoxynaphthalene (4.0 g) in dimethylformamide (15 ml) is added sodium hydride (60% dispersion-type) (404 mg) under ice-cooling, and the mixture is warmed to room temperature. The reaction mixture is stirred for 30 minutes, and cooled again with ice. To the reaction solution is added n-butyl iodide (2.2 g), and the mixture is warmed to room temperature and stirred overnight. The reaction solution is concentrated, and the resulting residue is dissolved in ethyl acetate, and washed with water. The mixture is dried and concentrated, and the resulting residue is subjected to silica gel column chromatography (eluent; hexane:ethyl acetate=3:1), and the desired fractions are concentrated to give 1-(N-butyl-2(1H)-pyridon-4-yl)-2,3-bis(methoxycarbonyl)-6,7-dimethoxynaphthalene (2.5 g) as crystal.

Yield: 55%

M.p. 144°–146° C.

As a side product, there is obtained 1-(2-butoxy-4-pyridyl)-2,3-bis(methoxycarbonyl)-6,7-dimethoxynaphthalene (1.4 g).

Yield: 31%

M.p. 112°–113° C. (crystallized from ethanol)

Reference Example 17

The corresponding pyridone-type starting compounds are treated in the same manner as in Reference Example 16 to give the compounds of Table 17.

TABLE 17

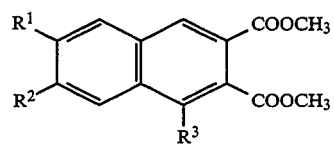

| Ref. Ex. No. | $R^1$ | $R^2$ | $R^3$ | Physical properties |
|---|---|---|---|---|
| 17-(1) | $CH_3O$ | $CH_3O$ | N-butyl-2-pyridon-4-yl | M.p. 144–146° C. |
| 17-(2) | $CH_3O$ | $CH_3O$ | 2-butoxy-4-pyridyl | M.p. 112–113° C. |
| 17-(3) | $CH_3CH_2O$ | $CH_3O$ | N-butyl-2-pyridon-4-yl | M.p. 129–131° C. |

TABLE 17-continued
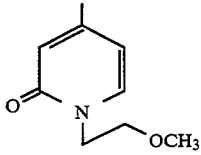
| Ref. Ex. No. | R¹ | R² | R³ | Physical properties |
|---|---|---|---|---|
| 17-(4) | $CH_3CH_2O$ | $CH_3O$ | 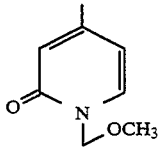 | M.p. 147–149° C. |
| 17-(5) | $CH_3CH_2O$ | $CH_3O$ | 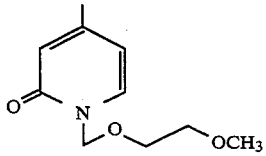 | M.p. 124–125° C. |
| 17-(6) | $CH_3CH_2O$ | $CH_3O$ | 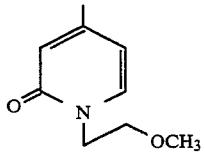 | Oil |
| 17-(7) | $CH_3CH_2O$ | $CH_3CH_2O$ | 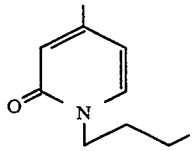 | M.p. 103–104° C. |
| 17-(8) | $CH_3CH_2O$ | $CH_3CH_2O$ | 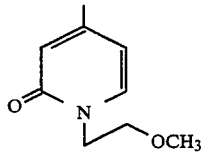 | M.p. 98–99° C. |
| 17-(9) | $CH_3O-\underset{\underset{O}{\parallel}}{C}-CH_2O$ | $CH_3O$ | 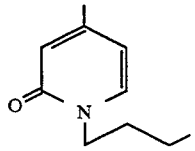 | M.p. 171–173° C. |
| 17-(10) | $CH_3O-\underset{\underset{O}{\parallel}}{C}-CH_2O$ | $CH_3O$ | 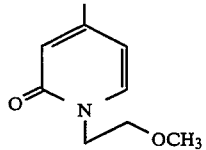 | M.p. 120–122° C. |
| 17-(11) | $CH_3OCH_2CH_2O$ | $CH_3O$ |  | M.p. 124–126° C. |

TABLE 17-continued

Structure: naphthalene with R¹ at 6-position, R² at 7-position, COOCH₃ at 2 and 3 positions, R³ at 1-position.

| Ref. Ex. No. | R¹ | R² | R³ | Physical properties |
|---|---|---|---|---|
| 17-(12) | CH₃O | CH₃CH₂O | 1-butyl-2-oxo-1,2-dihydropyridin-4-yl | M.p. 131–132° C. |
| 17-(13) | CH₃O | CH₃CH₂O | 1-(2-methoxyethyl)-2-oxo-1,2-dihydropyridin-4-yl | M.p. 167–168° C. |
| 17-(14) | CH₃O | C₆H₅CH₂O | 1-(2-methoxyethyl)-2-oxo-1,2-dihydropyridin-4-yl | Oil |
| 17-(15) | CH₃O | CH₃O—C(=O)—CH₂O | 1-(2-methoxyethyl)-2-oxo-1,2-dihydropyridin-4-yl | Oil |
| 17-(16) | CH₃O | CH₃OCH₂CH₂O | 1-(2-methoxyethyl)-2-oxo-1,2-dihydropyridin-4-yl | Oil |
| 17-(17) | CH₃O | CH₃OCH₂—CH₂OCH₂O | 1-(2-methoxyethyl)-2-oxo-1,2-dihydropyridin-4-yl | Oil |

Reference Example 18

(a) 6-Bromo-3,4-dimethoxybenzaldehyde dimethylacetal and acetaldehyde are treated in the same manner as in Reference Example 3 to give 3,4-dimethoxy-6-(1-hydroxyethyl)benzaldehyde dimethylacetal as oil.

(b) The above product is treated in the same manner as in Reference Example 8 to give 1-methyl-2,3-bis(methoxycarbonyl)-6,7-dimethoxynaphthalene. M.p. 142°–144° C.

(c) 1-Methyl-2,3-bis(methoxycarbonyl)-6,7-dimethoxynaphthalene is treated in the same manner as in Example 1 to give 1-methyl-2,3-bis(hydroxymethyl)-6,7-dimethoxynaphthalene. M.p. 180°–182° C.

(d) The above product is treated in the same manner as in Example 4 to give 1-methyl-2,3-bis(acetoxymethyl)-6,7-dimethoxynaphthalene.
M.p. 130°–131° C.

(e) To a solution of 1-methyl-2,3-bis(acetoxymethyl)-6,7-dimethoxynaphthalene (5.0 g) in carbon tetrachloride (100 ml) are added N-bromosuccinimide (2.8 g) and benzoyl peroxide (150 mg), and the mixture is refluxed for 2 hours. The mixture is allowed to cool, and the insoluble materials are separated by filtration, and the filtrate is concentrated under reduced pressure to give 1-bromomethyl-2,3-bis(acetoxymethyl)-6,7-dimethoxynaphthalene (5.1 g) as crystal.
Yield: 83%
M.p. 182°–183° C.

(f) To a solution of the above product (4.0 g) in chloroform (70 ml) is added tetrabutylammonium dichromate (8.8 g), and the mixture is refluxed for 2 hours. The mixture is allowed to cool, and then concentrated. The resulting residue is purified by silica gel column chromatography (eluent; n-hexane:ethyl acetate=2:1), and the fractions containing the desired compound are concentrated to give 1-formyl-2,3-bis(acetoxymethyl)-6,7-dimethoxynaphthalene (1.4 g) as crystal.

Yield: 41%

M.p. 154°–155° C.

(g) To a solution of the above product (5.0 g) in methylene chloride (30 ml) are added dropwise titanium chloride (1.7 ml) and 1-ethoxy-1-trimethylsilyloxycyclopropane (2.9 g) at −70° C. under nitrogen atmosphere. The reaction solution is gradually warmed, and stirred at 0° C. for one hour, and then thereto is added a saturated sodium chloride solution. The mixture is extracted with chloroform, and the chloroform layer is washed with water, and dried over magnesium sulfate. The mixture is concentrated, and the resulting residue is purified by silica gel column chromatography (eluent; hexane:chloroform:ethyl acetate=5:5:2, then hexane:ethyl acetate=1:1) to give 1-(1-hydroxy-3-ethoxycarbonylpropyl)-2,3-bis(acetoxymethyl)-6,7-dimethoxynaphthalene (4.0 g) as oil.

Yield: 62%

(h) To a suspension of pyridium chlorochromate (794 mg) in methylene chloride (10 ml) is added dropwise a solution of the above product (462 mg) in methylene chloride (5 ml) under ice-cooling. The mixture is warmed to room temperature, and reacted for three hours. To the mixture is added diethyl ether, and the mixture is separated by decantation. The resulting residue is subjected twice to decantation with diethyl ether, and further subjected twice to decantation with chloroform. The organic layers are combined, and filtered. The filtrate is concentrated, and the resulting residue is purified by silica gel column chromatography (eluent; hexane:chloroform:ethyl acetate=5:5:2). The desired fractions are concentrated to give 1-(1-oxo-3-ethoxycarbonylpropyl)-2,3-bis(acetoxymethyl)-6,7-dimethoxynaphthalene (400 mg) as crystal.

Yield: 87%

M.p. 85°–87° C.

Effects of the Invention

The desired compounds [I] of the present invention and pharmaceutically acceptable salts thereof have excellent bronchodilating activity, and are useful as medicines in the prophylaxis and treatment of asthma. That is, the desired compounds [I] of the present invention can effectively inhibit bronchoconstriction induced by various spasmogen or antigen such as histamine, U-46619, leukotriene D4, etc. For example, the desired compounds [I] wherein $R^1$ and $R^2$ are lower alkoxy group, $R^3$ is pyridyl group, N-alkyl-2(1H)-pyridonyl group or N-(lower alkoxy-lower alkyl)-2(1H)-pyridonyl group, a group of the formula: —$OR^4$ is hydroxy group or lower alkanoyloxy group, a group of the formula: —$OR^5$ is hydroxy group show 3 to 100 times as strong inhibitory activity on histamine-induced bronchoconstriction as theophylline.

Moreover, the desired compounds [I] of the present invention and pharmaceutically acceptable salts thereof hardly show any side effects on heart, and they show selectively bronchodilating activity as well as low-toxicity so that these compounds advantageously show high safety as medicaments. Although it is widely known that theophylline shows serious side effects on heart such as lowering blood pressure, palpitation, and the like, the desired compounds [I] of the present invention and pharmaceutically acceptable salts thereof do not show such side effects, but show excellent antiasthmatic activity.

What is claimed is:

1. A naphthalene compound of the formula (I):

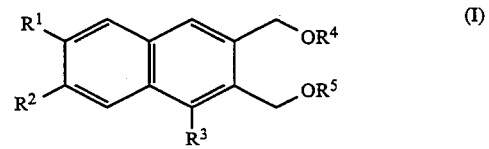

wherein $R^1$ and $R^2$ are the same or different and are (1) a hydrogen atom, (2) a hydroxy group, (3) a cyclopentyloxy group, (4) a lower alkoxy group which may optionally be substituted by a group selected from a hydroxy group, a lower alkoxy group, a lower alkoxy-lower alkoxy group, a lower alkoxycarbonyl group and a phenyl group, or (5) both combine to form a lower alkylenedioxy group, $R^3$ is a heterocyclic group selected from the group consisting of pyridin-2(or 6)-yl group, pyridin-3(or 5)-yl group, pyridin-4-yl group, (pyridine N-oxide)-2(or 6)-yl group, (pyridine N-oxide)-3(or 5)-yl group, (pyridine N-oxide)-4-yl group, 2(1H)-pyridon-3-yl group, 2(1H)-pyridon-4-yl group, 2(1H)-pyridon-5-yl group and 2(1H)-pyridon-6-yl group, said heterocyclic group optionally being substituted by a group selected from a fluorine atom, an alkoxy group and an alkyl group, wherein said alkoxy group and said alkyl group may optionally be substituted by a group selected from a hydroxy group, a lower alkoxy group, a lower alkoxy-lower alkoxy group, a lower alkylthio group, a lower alkenyl group, a cyano group, a carboxyl group, a lower alkoxycarbonyl group, an aminocarbyl group, a di-lower alkylamino group, a lower alkanoyl group, a phenyl group, a furyl group, a tetrahydrofuryl group and an oxazolyl group, and groups of the formulae: —$OR^4$ and —$OR^5$ are the same or different and are a protected or unprotected hydroxy group, or a pharmaceutically acceptable salt thereof.

2. The compound according to claim 1, wherein $R^3$ is (1) a heterocyclic group selected from the group consisting of pyridin-2(or 6)-yl group, pyridin-3(or 5)-yl group, and pyridin-4-yl group, said heterocyclic group optionally being substituted by a fluorine atom, (2) a heterocyclic group selected from the group consisting of (pyridine N-oxide)-2(or 6)-yl group, (pyridine N-oxide)-3(or 5)-yl group, (pyridine N-oxide)-4-yl group, 2(1H)-pyridon-3-yl group, 2(1H)-pyridon-4-yl group, 2(1H)-pyridon-5-yl group and 2(1H)-pyridon-6-yl group, or (3) a heterocyclic group selected from the group consisting of 2-alkoxy-3-pyridyl group, 2-alkoxy-4-pyridyl group, 2-alkoxy-5-pyridyl group, 2-alkoxy-6-pyridyl group, N-alkyl-2(1H)-pyridon-3-yl group, N-alkyl-2(1H)-pyridon-4-yl group, N-alkyl-2(1H)-pyridon-5-yl group and N-alkyl-2(1H)-pyridon-6-yl group, in which said alkoxy group and said alkyl group may optionally be substituted by a group selected from a hydroxy group, a lower alkoxy group, a lower alkoxy-lower alkoxy group, a lower alkylthio group, a lower alkenyl group, a cyano group, a carboxyl group, a lower alkoxycarbonyl group, a carbamoyl group, a di-lower alkylamino group, a phenyl group, a furyl group, a tetrahydrofuryl group, an oxazolyl group and an oxo group.

3. The compound according to any one of claims 1 and 2, wherein the groups of the formulae: —OR$^4$ and —OR$^5$ are the same or different, and are a hydroxy group which may optionally be protected by a group selected from a lower alkyl group and a lower alkanoyl group.

4. The compound according to any one of claims 2 and 3, wherein R$^1$ and R$^2$ are the same or different and are a lower alkoxy group, R$^3$ is pyridin-2-yl group, pyridin-3-yl group, pyridin-4-yl group, N-alkyl or N-(lower alkoxy-lower alkyl)-2(1H)-pyridon-3-yl group, N-alkyl or N-(lower alkoxy-lower alkyl)-2(1H)-pyridon-4-yl group, N-alkyl or N-(lower alkoxy-lower alkyl)-2(1H)-pyridon-5-yl group and N-alkyl or N-(lower alkoxy-lower alkyl)-2(1H)-pyridon-6-yl group, the group of the formula: —OR$^4$ is a hydroxy group which may optionally be protected by a lower alkanoyl group, and the group of the formula: —OR$^5$ is a hydroxy group.

5. A compound of the formula (II):

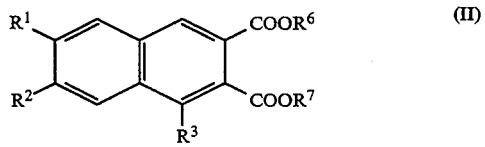

wherein R$^1$ and R$^2$ are the same or different and are (1) a hydrogen atom, (2) a hydroxy group, (3) a cyclopentyloxy group, (4) a lower alkoxy group which may optionally be substituted by a group selected from a hydroxy group, a lower alkoxy group, a lower alkoxy-lower alkoxy group, a lower alkoxycarbonyl group and a phenyl group, or (5) both combine to form a lower alkylenedioxy group, R$^3$ is a heterocyclic group selected from the group consisting of pyridin-2(or 6)-yl group, pyridin-3(or 5)-yl group, pyridin-4-yl group, (pyridine N-oxide)-2(or 6)-yl group, (pyridine N-oxide)-3(or 5)-yl group, (pyridine N-oxide)-4-yl group, 2(1H)-pyridon-3-yl group, 2(1H)-pyridon-4-yl group, 2(1H)-pyridon-5-yl group and 2(1H)-pyridon-6-yl group, said heterocyclic group optionally being substituted by a group selected from a fluorine atom, an alkoxy group and an alkyl group, wherein said alkoxy group and said alkyl group may optionally be substituted by a group selected from a hydroxy group, a lower alkoxy group, a lower alkoxy-lower alkoxy group, a lower alkylthio group, a lower alkenyl group, a cyano group, a carboxyl group, a lower alkoxycarbonyl group, an aminocarbonyl group, a di-lower alkylamino group, a lower alkanoyl group, a phenyl group, a furyl group, a tetrahydrofuryl group and an oxazolyl group, and the groups of the formulae: —COOR$^6$ and —COOR$^7$ are a free carboxyl group or an esterified carboxyl group, or an internal anhydride, or a salt thereof.

6. 1-[N-(2-methoxyethyl)-2(1H)-pyridon-4-yl]-2,3-bis(hydroxymethyl)-6,7-diethoxynaphthalene or a pharmaceutically acceptable salt thereof.

7. 1-[N-(2-methoxyethyl)-2(1H)-pyridon-4-yl]-2,3-bis(hydroxymethyl)-6-ethoxy-7-methoxynaphthalene or a pharmaceutically acceptable salt thereof.

8. A pharmaceutical composition which comprises as an active ingredient an effective amount of the compound as claimed in claim 1 in admixture with a pharmaceutically acceptable carrier or diluent.

9. A method for the treatment or prophylaxis of asthma in a warm-blooded animal which comprises administering an effective amount of the compound as claimed in claim 1 to said warm-blooded animal.

* * * * *

UNITED STATES PATENT AND TRADEMARK OFFICE
CERTIFICATE OF CORRECTION

PATENT NO. : 5,342,941
DATED : August 30, 1994
INVENTOR(S) : Tameo Iwasaki et al.

It is certified that error appears in the above-indentified patent and that said Letters Patent is hereby corrected as shown below:

Claim 1, column 58, line 40 change "carbyl" to --carbonyl--.

Signed and Sealed this

Twentieth Day of December, 1994

*Attest:*

BRUCE LEHMAN

*Attesting Officer*  *Commissioner of Patents and Trademarks*